US004001704B2

United States Statutory Invention Registration [19]

[11] Reg. Number: H1704

Wallajapet et al.

[45] Published: Jan. 6, 1998

[54] MODIFIED CELLULOSE FIBER HAVING IMPROVED CURL

[75] Inventors: Palani Raj Ramaswami Wallajapet, Wauwatosa; Ramakant Tukaram Shet, Neenah, both of Wis.

[73] Assignee: Kimberly-Clark Worldwide, Inc., Neenah, Wis.

[21] Appl. No.: 766,249

[22] Filed: Dec. 13, 1996

[51] Int. Cl.[6] ..... C08B 5/00

[52] U.S. Cl. ..... 536/30

[56] References Cited

U.S. PATENT DOCUMENTS

| | | | |
|---|---|---|---|
| 4,898,642 | 2/1990 | Moore et al. | 162/157.6 |
| 5,522,967 | 6/1996 | Shet | 162/9 |

OTHER PUBLICATIONS

Neogi, A. N. and Jon R. Jensen, "Wet Strength Improvement Via Fiber Surface Modification," Tappi, vol. 63, No. 8, Aug. 1980, pp. 86–88.

TAPPI Official Test Method T237 om–93, "Carboxyl Content of Pulp," published by the TAPPI Press, Atlanta, Georgia, revised 1993, pp. 1–3.

TAPPI Official Test Method T430 om–94, "Copper Number of Pulp, Paper and Paperboard," published by the TAPPI Press, Atlanta, Georgia, revised 1994, pp. 1–3.

*Primary Examiner*—Charles T. Jordan
*Assistant Examiner*—Meena Chelliah
*Attorney, Agent, or Firm*—John R. Schenian

[57] ABSTRACT

Disclosed is a modified cellulose fiber having improved curl characteristics. Specifically, the present invention relates to oxidized or sulfonated cellulose fibers being highly curled, wherein such curl is highly stable. The oxidized or sulfonated curled cellulose fiber may be prepared by a process comprising treating the fibers in a high energy refiner effective to provide the desired curl properties to the fiber. The modified cellulose having improved curl characteristics may be used in disposable absorbent products.

12 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

MODIFIED CELLULOSE FIBER HAVING IMPROVED CURL

BACKGROUND OF THE INVENTION

1. Field of the Invention

The present invention relates to modified cellulose fibers having improved curl characteristics. Specifically, the present invention relates to oxidized or sulfonated cellulose fibers being highly curled, wherein such curl is highly stable.

2. Description of the Related Art

The use of cellulosic fibers in products is well known. For example, cellulosic fibers may be used in paper products including bags, tags, toweling, tissue, map papers, paper patterns, napkins, poster papers, filter papers, and many other grades or uses of paper. It is also known to use cellulosic fibers in structures or components of disposable absorbent products such as diaper liners, diaper wrap sheets, diaper absorbent structures, feminine napkin wrap sheets, disposable hospital bed pads, and the like.

Many products prepared from cellulosic fibers absorb liquids or otherwise become wet during use. It is generally desirable that the product, upon absorbing a liquid or otherwise becoming wet during use, substantially exhibit the same properties as when the product was dry. However, many cellulosic fibers are not stable upon absorbing a liquid or otherwise becoming wet losing, for example, their shape, resiliency, stiffness, or strength. Thus the use of such wet-unstable cellulosic fibers in preparing a product will generally not result in a product that exhibits the same properties when wet as when the product was dry.

It is therefore desirable to develop and produce a cellulosic fiber having desirable properties in both dry and wet conditions and which, thus, is suitable for use in products such as personal care absorbent products.

SUMMARY OF THE INVENTION

In one aspect, the present invention concerns an oxidized or sulfonated cellulose fiber. The oxidized or sulfonated cellulose fiber is characterized in that it is highly curled, wherein such curls are substantially stable, particularly when the fiber is wet.

One embodiment of the present invention concerns an oxidized or sulfonated cellulose fiber having a curl factor greater than about 6 wherein the curls are substantially stable in water.

In another aspect, the present invention concerns a process for preparing an oxidized or sulfonated cellulose fiber, wherein the prepared cellulose fiber is highly curled and wherein such curls are substantially stable, particularly when the fiber is wet.

In one embodiment, the process comprises treating an oxidized or sulfonated cellulose fiber in a high energy refiner effective to provide desired curl properties to the fiber.

DETAILED DESCRIPTION OF THE PREFERRED EMBODIMENTS

It has now been discovered that cellulose fiber can be modified by oxidation or sulfonation and subsequently treated in a high energy refiner to provide desired curl properties to the fiber. In accordance with this invention, the high-energy refining of oxidized or sulfonated cellulose fibers to an effective level of stable curls results in significant and unexpected improvements in the properties of the modified cellulose fiber.

As used herein, an oxidized cellulose is intended to refer to a cellulose chain that has any combination of aldehyde or carboxyl functionalities present at any of or all of the carbon atoms at the 2, 3, or 6 positions of cellulose or any combinations thereof.

The oxidized cellulose of the present invention can be characterized by an aldehyde content determined by copper number, with a copper number beneficially from about 0.05 gram to about 20 grams, suitably from about 1 gram to about 15 grams, and more suitably from about 5 gram to about 10 grams per 100 grams of cellulose.

As used herein, the "copper number" is meant to represent a measure of the reducing groups in celllose and may be used to obtain a measure of the aldehyde content of a cellulose. Specifically, the copper number is defined as the number of grams of metallic copper oxide ($Cu_2O$) resulting from the reduction of copper sulfate ($CuSO_4$) by 100 grams of cellulose. The copper number may be determined using TAPPI standardized test method T 430 om-94, published by the TAPPI Press, Atlanta, Ga., hereby incorporated herein in its entirety by reference.

The carboxyl group content of the oxidized cellulose of the present invention can range beneficially from about 1 milliequivalent to about 100 milliequivalents, suitably from about 5 milliequivalents to about 70 milliequivalents, and more suitably from about 20 milliequivalents to about 50 milliequivalents per 100 grams of cellulose. The carboxyl group content of an oxidized cellulose can be determined by reaction of the oxidized cellulose with sodium bicarbonate/sodium chloride solution and titration with dilute hydrochloric acid. The carboxyl group content of the oxidized cellulose may be determined using TAPPI standardized test method T 237 om-93, published by the TAPPI Press, Atlanta, Ga., hereby incorporated herein in its entirety by reference.

As used herein, a sulfonated cellulose is intended to refer to a hydroxy sulfonic cellulose in which both the sulfur atom of a sulfonic group and a hydroxyl group are directly attached to a carbon atom on the cellulose chain. The sulfonic group may generally be present in the acid form or in the neutralized or salt form. The hydroxy sulfonic acid functionality can generally be attached to any or all of the carbon atoms at the 2, 3, or 6 positions of cellulose Or any combinations thereof. The carbon atoms at the 2, 3, or 6 positions of cellulose which are not substituted with hydroxy sulfonic acid can generally have an aldehyde functionality, a hydroxyl functionality, a carboxyl functionality or any combinations thereof. Representative structures of sulfonated cellulose include, but are not limited to, the following:

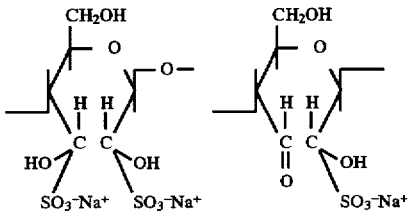

-continued

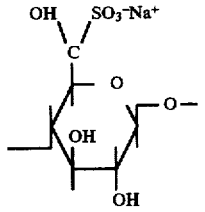

As such, the sulfonated cellulose of the present invention differs from other sulfur containing cellulose compounds in which the sulfur atom is indirectly connected to a carbon atom on the cellulose chain as, for example, in the case of cellulose alkyl sulfonates.

As used herein, "sulfonated cellulose" is not to be confused with "sulfonated pulp," the latter being the basis for the many varieties of sulfite pulping processes and most of the chemithermomechanical pulping processes. When sulfonating pulp, it is the lignin portion of the pulp that is sulfonated rather than the cellulose portion. Sulfonation of lignin serves to soften the lignin and/or make it soluble under suitable conditions in the form of sulfonated lignin or a ligno-sulfonate. In the case of chemithermomechanical pulping or its variations, the objective of the sulfonation has been to soften the lignin by sulfonation so that individual fibers can be separated from the mass with minimal damage to the fibers. The fiber separation is accomplished by mechanical means with thermal assistance to the sulfonation in softening the lignin binding individual fibers together. No attempt is made to dissolve or remove the lignin. In full chemical pulping by the sulfite process or one of its variations, the lignin is sulfonated under suitable conditions so that the lignin is dissolved and removed from the fiber as a ligno-sulfonate.

The sulfonated cellulose of the present invention can be characterized by an average degree of sulfonic group substitution beneficially of from about 0.001 to about 0.2, suitably from about 0.0025 to about 0.1, and more suitably from about 0.005 to about 0.015. As used herein, the "average degree of sulfonic group substitution" is the average moles of sulfonic groups per mole of glucose unit in the cellulose. The maximum degree of sulfonic group substitution that can be obtained is 3 when all hydroxyl groups in the glucose residue are oxidized to dialdehyde and subsequently converted to sulfonates.

Cellulosic materials with a wide range of degree of polymerization are generally suitable for making the modified cellulose materials of the present invention. It is often beneficial to use cellulosic materials with a relatively high degree of polymerization. Cellulosic material suitable for use in the present invention will suitably have a degree of polymerization greater than about 100, more suitably greater than about 500, and most suitably greater than about 1000.

It has been found to be possible to produce an improvement in curl properties in oxidized or sulfonated cellulose fiber over a wide range of molecular weights. While high molecular weight modified cellulose fibers are generally preferred, it is important that improvements in curl properties in low molecular weight modified cellulose fibers can also be achieved. For reasons of efficiency, it is often desirable to form an aqueous dispersion comprising the highest concentration of modified cellulose fiber possible while still being able to effectively work with the aqueous dispersion.

The oxidized or sulfonated cellulose fiber of the present invention has been found to exhibit a desired amount of fiber curl. As used herein, the curl of a fiber is meant to represent the fractional shortening of a fiber due to kink, twists, and/or bends in the fiber and is referred to herein as the curl factor of a fiber.

The curl factor of a fiber may be measured by dispersing a sample of fibers in water and transferring the fibers onto a 2 inch by 6 inch glass slide and then diluting the fibers effective to observe individual fibers. A fiber image analysis system, available from Leica Cambridge Ltd., Cambridge, England, under the designation Quantimet 900 image analysis system, was used herein to perform the image analysis measurements. The fibers were imaged using a scan stage and actual length ($L_a$) and maximum projected length ($L_r$) of the fibers was measured. The Curl Factor value of a fiber is obtained by calculating the ratio $L_a/L_r$.

The oxidized or sulfonated cellulose fiber of the present invention exhibits a Curl Factor value that is beneficially at least about 6, more beneficially at least about 7, suitably at least about 8, more suitably at least about 9, and most suitably at least about 10.

It is desired that the oxidized or sulfonated cellulose fiber of the present invention exhibits a Curl Factor value that is substantially stable when the fiber is wet. Fibers that do not have wet-stable curls tend to uncurl upon wetting. The test method used for measuring the Curl Factor value herein allows the fibers to be in contact with water for about 30 minutes before length measurements are made. Thus, the method used for determining the Curl Factor value measured the curl of a fiber under wet conditions and is a measure of wet curl stability.

Modified cellulose fibers exhibiting an effective Curl Factor value, such as of at least about 6, have been found, for example, to exhibit lower water retention values, higher wet and dry resiliency, and superior fluid intake properties as compared to modified cellulose fibers that do not exhibit an effective Curl Factor value. It has also been found that the curled modified cellulose fibers of the present invention generally exhibit a relatively cylindrical morphology as compared to the flat ribbon-like morphology exhibited by unmodified and/or uncurled cellulose fibers.

The water retention value of a fiber is intended to represent the ability of a fiber to retain an absorbed liquid after being subjected to a centrifugal force for a period of time. The water retention value of a fiber sample may be measured by dispersing about 0.5 gram of a fiber sample into about 200 milliliters of deionized water using a Waring blender at the low setting for about 30 seconds. The slurry is then transferred to a beaker and allowed to stand for about 16 hours. The water is then decanted and the fiber sample is placed in a centrifuge tube and then centrifuged for about 20 minutes at about 958.5 times the gravitational force. The weight of the fiber sample after centrifuging ($W_1$) is measured. The fiber sample is then dried at about 105° C. for about 2 hours. The weight of the fiber sample after drying ($W_2$) is measured. The weight of the water retained after centrifuging ($W_1-W_2$) per gram of dry fiber sample ($W_2$) is calculated as $(W_1-W_2)/W_2$ from the data obtained, and this is expressed as the Water Retention value in terms of grams of water retained per gram of dry fiber sample.

It has been found that the oxidized or sulfonated cellulose fiber of the present invention may be prepared by simple processes. In general, the method of making oxidized cellulose fiber comprises the step of oxidizing cellulose fiber with an oxidizing agent to form aldehydo or carboxyl cellulose. In general, the method of making sulfonated cellulose fiber comprises the steps of (a) oxidizing cellulose fiber with an oxidizing agent to form aldehydo cellulose; and (b) sulfonating the oxidized cellulose with a sulfonation agent to form sulfonated cellulose.

With regard to the oxidation reaction, there are a great many ways in which the chain units in cellulose can be oxidized. However, most oxidants are unspecific in their mode of attack. Suitable oxidants for purposes of this invention include, without limitation, sodium metaperiodate, sodium paraperiodate, periodic acid, sodium hypochlorite, hydrogen peroxide, ozone, potassium dichromate, potassium permanganate, and sodium chlorite. Periodate ions react with the cellulose without destroying its fibrous nature and result primarily in the oxidative scission of 1,2-diols to primarily produce dialdehyde oxycellulose under proper conditions. For this reason the preferred oxidizing agents are the periodates, such as sodium metaperiodate ($NaIO_4$).

The temperature of the oxidation reaction can suitably be from about 20° C. to about 55° C., more suitably from about 30° C. to about 50° C., and most suitably from about 35° C. to about 40° C. At temperatures below about 20° C., the oxidation reaction generally proceeds too slowly to be practical. At temperatures greater than 55° C., the oxidation of cellulose generally proceeds too fast and causes nonuniformity of the product and of the cellulose.

The pH of the oxidation reaction can suitably be from about 2 to about 7, more suitably from about 3 to about 6.5, and most suitably from about 3 to about 5. When using sodium metapedodate, for example, it is generally desirable to use a pH that is between about 3 to about 4.6 since at a higher pH, the sodium metaperiodate is generally converted to insoluble paraperiodate.

If sodium metaperiodate is used as the oxidation agent, the upper concentration of sodium metaperiodate is generally limited by its solubility in water, which is about 14.44 grams per 100 milliliters at 25° C. The maximum concentration of sodium metaperiodate which can therefore be achieved is about 0.67M. On the other hand, at concentrations of sodium metaperiodate below about 0.005M the rate of reaction is generally too slow for the oxidation process to be economically feasible. Suitable concentrations of sodium metaperiodate are from about 0.01M to about 0.2M. At higher concentrations, although the oxidation reaction will proceed faster toward the desired degree of substitution, the shorter treatment time is likely to result in non-uniformity of the substitution.

With regard to the sulfonation reaction, suitable sulfonation reagents include, without limitation, alkali bisulfite, such as sodium bisulfite, and a combination of sodium hydroxide and sulfur dioxide. A preferred reagent is sodium bisulfite ($NaHSO_3$). The concentration of sodium bisulfite is generally not critical provided there is an excess over the stoichiometric amount required. When using sodium bisulfite as the sulfonation agent, the concentration of the sodium bisulfite is suitably from about 1 to about 10 weight percent, more suitably from about 2 to about 5 weight percent, based on the weight of the cellulose fiber.

The temperature of the sulfonation reaction is suitably from about 25° C. to about 90° C. or greater, more suitably from about 25° to about 35° C.

The pH of the sulfonation reaction is suitably from about 3 to about 4.5. Although the sulfonation reaction generally proceeds faster at lower pH levels, sulfur dioxide will be lost unless the reaction is carried out under pressure. Also, at high temperatures and acidic pH, cellulose is likely to undergo hydrolyric degradation.

A suitable method of making oxidized cellulose or sulfonated cellulose is to oxidize cellulose pulp with sodium metaperiodate at a concentration above about 0.01M for over about one hour at about room temperature or above. The oxidized cellulose thus produced is then suitably washed with water to remove any soluble reaction agents or products. The recovered oxidized cellulose may then be treated to impart the desired curl to the oxidized cellulose. Alternatively, the recovered oxidized cellulose may be suitably reacted with a greater than about 0.3 percent aqueous solution of sodium bisulfite at ambient temperature or higher for about one hour at a pH of about 4.5 to prepare a sulfonated cellulose. The product is then washed again to remove unreacted sodium bisulfite and any soluble reaction products. The prepared sulfonated cellulose may be used as is in a never dried condition or partially dried by conventional means and then treated to impart the desired curl to the sulfonated cellulose.

The method of preparation of sulfonated cellulose is shown, for example, in U.S. Pat. No. 5,522,967, by Ram Shet, issued Jun. 4, 1996, and in pending U.S. patent application Ser. No. 08/571,332, filed Dec. 13, 1995, by R. Shet and R. Wallajapet, the disclosures of which are hereby incorporated herein in their entirety by reference.

The oxidation and subsequent sulfonation of cellulose can be carried out on a wide variety of raw materials including celluloses derived from both woody and non-woody plants, coniferous as well as deciduous trees, and by a variety of pulping processes including Kraft, Soda, a variety of sulfite processes, and chemithermomechanical pulping. Secondary fiber obtained by recycling waste paper would also be suitable as a raw material for oxidation and sulfonation.

The oxidation/sulfonation can also be carried out on any of the above-mentioned celluloses that have been mechanically refined prior to the oxidation/sulfonation process. When used as a pretreatment, refining serves to bring about external and internal fibrillation of the cellulose fibers. This increases the surface area of the fibers and also increases accessibility of the fibrils and cellulose chains to oxidation/sulfonation.

Cellulose is generally known to be a highly crystalline material. The degree of crystallinity generally depends on the source of the cellulose and its processing history. The highly-ordered crystalline structures and the less-ordered amorphous areas generally have different accessibilities to oxidizing and sulfonating agents. The result of this difference in accessibility is that the amorphous areas and surface of crystallites are, in the case of reaction with an oxidizing agent, generally oxidized first and heaviest, whereas the highly crystalline areas are oxidized last and least. Swelling of the cellulose improves the accessibility of the oxidizing agent into the crystalline areas and facilitates the oxidation. Any other process that would increase accessibility, including the use of never dried pulp, would also generally be beneficial. In general, it is observed that the crystallinity of a sulfonated cellulose decreases with an increasing degree of sulfonic group substitution.

Cellulose suitable for use in the present invention is generally without a substantial amount of curl prior to oxidation and/or sulfonation and subsequent high-energy refining of the cellulose to provide the curled oxidized or sulfonated cellulose as disclosed herein. After such treatment processes, the oxidized or sulfonated cellulose will generally exhibit a desired level of stable curl. It is believed that the modification of the cellulose by oxidation and/or sulfonation generally reduces the softening temperature of the cellulose, thereby making the cellulose more conformable and pliable. Such an increase in the conformability of the modified cellulose fibers generally results in the modified cellulose fibers being favorable to the development of curl by the application of mechanical energy. Such a change in the softening properties of the cellulose is thus utilized in the present invention to achieve a high curl factor in the modified cellulose by the method of mechanical dispersing. As such, the process of the present invention generally does not require the use of any additives to the cellulose fibers during the curling process or any post-treatment steps, such as curing or similar heat-treatments, after the dispersing treatment of the fibers to achieve the desired curls. It is believed that the modified cellulose fibers of the present invention are capable of forming in situ linkages, such as hemiacetal, acetal, ester, or ionic, during the dispersing process and that such linkages result in the stabilization of the curl of the fibers.

Thus, after recovery from the oxidation and/or sulfonation process, the modified cellulose fiber is generally prepared as an aqueous pulp and then treated with a high-energy refining process to achieve a desired amount of fiber curl. The curling of the modified cellulose herein can generally be achieved by using a curlator which provides significant fiber-to-fiber contact and is capable of imparting sufficient energy to curl the fibers. A suitable method of curling the modified fibers includes the use of suitable shaft dispersers. A variety of shaft dispersers or equivalent mechanical devices are believed capable of being suitable to obtain the desired amount of curl in the modified fibers of the present invention. Suitable shaft dispersers include, without limitation, nonpressurized shaft dispersers and pressurized shaft dispersers. The consistency of the cellulose pulp subjected to dispersing must generally be sufficiently high to provide effective fiber-to-fiber contact. As such, the modified cellulose is present in a pulp beneficially from about 20 to about 60 weight percent, suitably from about 25 to about 55 weight percent, and more suitably from about 30 to about 50 weight percent, based on the total weight of the cellulose pulp.

The temperature used during the high-energy refining process may generally be at any effective temperature, but is beneficially greater than about 25° C., suitably greater than about 40° C., more suitably greater than about 75° C. and most suitably greater than about 100° C. In general, the upper limit for the temperature used in the process is dependent on the equipment being used and if such equipment can be pressurized since at sufficiently high temperatures the water in the cellulose pulp will boil. However, it is generally desirable to use as high of a temperature as is possible since the use of higher temperatures has been found to generally result in improved curl of the modified fibers as compared to the use of lower temperatures.

A typical high-energy disperser is a shaft disperser, available from Ing. S. Maule & C. S.p.A., Torino, Italy, under the designation type GR II shaft disperser. Such a device comprises an upper cylindrical housing and lower cylindrical housing which when closed encloses a rotating shaft provided with a multiplicity of arms. The upper cylindrical housing has three rows of knurled fingers, three inspection ports and an inlet port at one end. A drive motor for turning the shaft is provided at the inlet end along with a bearing assembly at the outlet end. The inlet end of the rotating shaft has a screw feed section to move the pulp coming through the inlet port into the disperser. At the outlet end of the disperser is a hinged flap to adjust the outlet opening from the disperser. The opening of the hinged flap is controlled by air bags and this is used to adjust the back pressure in the disperser. Increasing the back pressure in the disperser increases the degree to which the fibers are worked, leading to a higher curl factor. Steam can be injected into the feed stream to elevate the dispersing temperature. However, because of the limitations of this disperser, it is generally not possible to impart a sufficient amount of energy onto the modified fibers being treated with this disperser such that the modified fibers will generally not exhibit the desired Curl Factor values as described herein.

A high-energy disperser suitable for use in the present invention is a machine available from Clextral Company, Firminy Cedex, France, under the designation Bivis high-energy disperser. The Bivis machine is a twin screw disperser. Pulp is introduced through an inlet where it encounters a short feed screw. The feed screw transfers the pulp to a first working zone. The working zone consists of a pair of intermeshing screws which are enclosed in a cylindrical housing. The screws co-rotate to transport the pulp axially through the disperser. High energy dispersing is achieved by using reverse-flighted screws which have small slots machined in the flights. Reverse-flighted screws are positioned periodically along the length of both screws and serve to reverse the flow of pulp through the machine, thereby introducing back pressure. Pressure builds up in this zone and forces the pulp to flow through the slots in the reverse flights into the next forward flighted screw section which is at a lower pressure. This compression/expansion action imparts a high energy to the pulp during dispersion. Steam can be injected into the pulp to carry out high temperature dispersing. This disperser has been found to generally be capable of imparting a sufficient amount of energy onto the modified fibers being treated with this disperser such that the treated modified fibers will generally exhibit the desired Curl Factor values as described herein.

The curled modified cellulose of the present invention is suitable for use in products requiring cellulose fibers that are substantially wet stable, such as disposable absorbent products such as personal care products, such as diapers, training pants, baby wipes, feminine care products, adult incontinent products, and medical products, such as wound dressings or surgical capes or drapes. When the modified, curled cellulose of the present invention is intended for use in disposable absorbent products, it is typically desired that the modified cellulose have a generally neutral or slightly acidic character.

In one embodiment of the present invention, a disposable absorbent product is provided, which disposable absorbent product comprises a liquid-permeable topsheet, a backsheet attached to the topsheet, and an absorbent structure positioned between the topsheet and the backsheet wherein the absorbent structure comprises the modified cellulose of the present invention, wherein the modified cellulose exhibits desired curl characteristics.

Those skilled in the art will recognize materials suitable for use as the topsheet and backsheet. Exemplary of materials suitable for use as the topsheet are liquid-permeable materials, such as spunbonded polypropylene or polyethylene having a basis weight of from about 15 to about 25 grams per square meter. Exemplary of materials suitable for use as the backsheet are liquid-impervious materials, such as polyolefin films, as well as vapor-pervious materials, such as microporous polyolefin films.

Disposable absorbent products, according to all aspects of the present invention, are generally subjected during use to multiple insults of a body liquid. Accordingly, the disposable absorbent products are desirably capable of absorbing multiple insults of body liquids in quantities to which the absorbent products and structures will be exposed during use. The insults are generally separated from one another by a period of time.

Test Methods

Curl Factor

The Curl Factor is a test which measures the fractional shortening of a fiber due to kink, twists, and/or bends in the fiber. For the purposes of this invention, a fiber's Curl Factor is measured in terms of a two dimensional plane, determined by viewing the fiber in a two dimensional plane. To determine Curl Factor, the projected length of a fiber as the longest dimension of a two dimensional rectangle encompassing the fiber, $L_r$, and the actual length of the fiber, $L_a$, are both measured. An image analysis method may be used to measure $L_r$ and $L_a$. A suitable image analysis method is described in U.S. Pat. No. 4,898,642, hereby incorporated herein in its entirety by reference. The fiber Curl Factor can then be calculated from the following equation:

$$\text{Curl Factor}=L_aL_r$$

Sulfonic Group Substitution

The sulfur content of a treated cellulose material may be determined by elemental sulfur analysis and may be expressed as a weight percent of the cellulose material. The sulfonic group substitution of a sulfonated cellulose material is 0.05 times the percent sulfur content. In addition to elemental sulfur analysis, energy dispersive x-ray analysis may be used to confirm the presence of sulfur in the sulfonated cellulose material.

EXAMPLES

About 150 pounds of sodium metaperiodate was dissolved in about 1500 gallons of water in a high-consistency pulper. The pH of the solution was adjusted to about 4.5 using dilute sulfuric acid. About 1500 pounds of southern softwood kraft pulp was added to the pulper. A sample of the southern softwood kraft pulp was evaluated and exhibited a Curl Factor of about 1.4 and a Water Retention value of about 0.94 gram/gram.

The treatment of the pulp with sodium periodate solution was performed at about 30° C. for about one hour. The pulp slurry was then diluted to about 3 weight percent consistency with water and filtered. The filtered pulp was washed by diluting to about 3 weight percent consistency with water, agitating the slurry for about 30 minutes and filtering the pulp. The pulp washing step was repeated 3 times and the washed pulp was obtained at about 30 weight percent consistency.

The oxidized pulp obtained from the earlier step was then sulfonated in a second step. The pulp from the earlier step was added to about 1100 gallons of water in a high consistency pulper and agitated for about 20 minutes. About 75 pounds of sodium bisulfite was added to the pulp slurry and the reaction was done at about 25° C. for about one hour. The pulp was then diluted to about 3 weight percent consistency with water and filtered. The filtered pulp was washed by diluting to about 3 weight percent consistency with water, agitating the slurry for about 20 minutes and filtering the pulp. The pulp washing step was repeated 6 times and the washed sulfonated pulp was obtained at about 30 weight percent consistency. A sample of the sulfonated pulp was evaluated and exhibited a Curl Factor of about 2.1 and a Water Retention value of about 2.2 grams/gram.

A portion of the prepared sulfonated pulp, at about 30 weight percent consistency, was fed to a high-energy disperser, available from Clextral Company, Firminy Cedex, France, under the designation Bivis high-energy disperser. The disperser was maintained at a temperature of about 98° C. by using steam. The power input to the disperser was maintained at about 6.0 horsepower-day per ton of fiber and the feed rate of the pulp was about 2000 pounds per hour. A sulfonated pulp at about 42 weight percent consistency was obtained. A sample of the treated sulfonated pulp was evaluated and exhibited a Curl Factor of about 7.8 and a Water Retention value of about 0.59 gram/gram. As a comparative, a sample of the original southern softwood kraft pulp was treated in the Bivis high-energy disperser under similar conditions to those disclosed above. The treated southern softwood kraft pulp was evaluated and exhibited a Curl Factor of about 2.7 and a Water Retention value of about 0.94 gram/gram.

As another comparative, a second portion of the prepared sulfonated pulp, at about 30 weight percent consistency, was fed to a shaft disperser, available from Ing. S. Maule & C. S.p.A., Torino, Italy, under the designation type GR II shaft disperser. The disperser was maintained at a temperature of about 80° C. by using steam. The power input to the disperser was maintained at about 2.0 horsepower-day per ton of fiber and the feed rate of the pulp was about 1000 pounds per hour. About 600 pounds of sulfonated pulp at about 32 weight percent consistency was obtained. A sample of the treated sulfonated pulp was evaluated and exhibited a Curl Factor of about 2.9 and a Water Retention value of about 0.72 gram/gram. As another comparative, a sample of the original southern softwood kraft pulp was treated in the Maule disperser under similar conditions to those disclosed above. The treated southern softwood kraft pulp was evaluated and exhibited a Curl Factor of about 2.1 and a Water Retention value of about 0.94 gram/gram.

While the present invention has been described in terms of the specific embodiments described above, numerous equivalent changes and modifications will be clear to those skilled in the art. Accordingly, the specific examples set forth above are not intended to limit in any manner the scope of the invention as set forth in the appended claims.

What is claimed is:

1. An oxidized cellulose fiber exhibiting a Curl Factor value that is at least about 6.

2. The oxidized cellulose fiber of claim 1 wherein the oxidized cellulose fiber exhibits a Curl Factor value that is at least about 7.

3. A sulfonated cellulose fiber exhibiting a Curl Factor value that is at least about 6.

4. The sulfonated cellulose fiber of claim 3 wherein the sulfonated cellulose fiber exhibits a Curl Factor value that is at least about 7.

5. A process for treating an oxidized cellulose fiber, the process comprising treating an oxidized cellulose fiber in a refining means wherein the refining means is operated at a power input of greater than about 2 horsepower-day per ton of oxidized cellulose fiber, wherein the treated oxidized cellulose fiber exhibits a Curl Factor value that is at least about 6.

6. The process of claim 5 wherein the treated oxidized cellulose fiber exhibits a Curl Factor value that is at least about 7.

7. The process of claim 5 wherein the power input to the refining means is greater than about 6 horsepower-day per ton of oxidized cellulose fiber.

8. The process of claim 5 wherein the oxidized cellulose fiber is treated in the refining means as a pulp comprising water and between about 20 to about 60 weight percent of the oxidized cellulose fiber.

9. A process for treating a sulfonated cellulose fiber, the process comprising treating an sulfonated cellulose fiber in a refining means wherein the refining means is operated at a power input of greater than about 2 horsepower-day per ton of sulfonated cellulose fiber, wherein the treated sulfonated cellulose fiber exhibits a Curl Factor value that is at least about 6.

10. The process of claim 9 wherein the treated sulfonated cellulose fiber exhibits a Curl Factor value that is at least about 7.

11. The process of claim 9 wherein the power input to the shaft disperser is greater than about 6 horsepower-day per ton of sulfonated cellulose fiber.

12. The process of claim 9 wherein the sulfonated cellulose fiber is treated in the refining means as a pulp comprising water and between about 20 to about 60 weight percent of the sulfonated cellulose fiber.

* * * * *